US012133591B2

(12) United States Patent
Lee et al.

(10) Patent No.: US 12,133,591 B2
(45) Date of Patent: Nov. 5, 2024

(54) ADAPTER WITH INTERCHANGEABLE ELEMENT FOR CONNECTING MAKEUP APPLICATOR TO AN EXTERNAL DEVICE

(71) Applicant: L'OREAL, Paris (FR)

(72) Inventors: Ji Lee, New York, NY (US); Guive Balooch, New York, NY (US)

(73) Assignee: L'Oreal, Paris (FR)

( * ) Notice: Subject to any disclaimer, the term of this patent is extended or adjusted under 35 U.S.C. 154(b) by 912 days.

(21) Appl. No.: 17/036,597

(22) Filed: Sep. 29, 2020

(65) Prior Publication Data

US 2022/0095775 A1 Mar. 31, 2022

(51) Int. Cl.
| | | |
|---|---|---|
| *A46B 11/00* | (2006.01) |
| *A46B 5/00* | (2006.01) |
| *A46B 5/02* | (2006.01) |
| *A46B 13/08* | (2006.01) |
| *A46B 15/00* | (2006.01) |
| *A61F 4/00* | (2006.01) |

(Continued)

(52) U.S. Cl.
CPC .......... *A46B 5/0079* (2013.01); *A46B 5/0095* (2013.01); *A46B 5/025* (2013.01); *A46B 13/08* (2013.01); *A46B 15/0004* (2013.01); *A61F 4/00* (2013.01); *F16B 21/02* (2013.01); *A46B 13/001* (2013.01); *A46B 2200/1046* (2013.01)

(58) Field of Classification Search
CPC ..... A46B 5/0079; A46B 5/0095; A46B 5/025; A46B 13/08; A46B 15/004; A61F 4/00; F16B 21/02
See application file for complete search history.

(56) References Cited

U.S. PATENT DOCUMENTS

| 10,420,663 B2 | 9/2019 | Pathak et al. |
| 10,758,388 B2 | 9/2020 | Pathak et al. |
| 11,369,500 B2 * | 6/2022 | Pathak ..................... A61F 4/00 |
| | (Continued) |

FOREIGN PATENT DOCUMENTS

| CN | 206198073 U | 5/2017 |
| CN | 110368124 A | 10/2019 |
| | (Continued) |

OTHER PUBLICATIONS

French Preliminary Search Report issued Nov. 26, 2020 in Patent Application No. FR2012204 (with English translation of categories of cited documents), 5 pages.

(Continued)

*Primary Examiner* — Jennifer C Chiang
(74) *Attorney, Agent, or Firm* — Christensen O'Connor Johnson Kindness PLLC

(57) ABSTRACT

An adapter is provided that connects any one of a variety of makeup applicators for applying makeup to a motion controlling device that directs movement of the makeup applicator. The adapter includes a base component having a base connection for connecting the adapter to the motion controlling device in a certain orientation, and an end component having an end connection for connecting the adapter to a makeup applicator. The end component has a center axis through its center and is rotatably attached about the center axis to the base component with a structure for locking the end component in a certain rotated angle about the center axis.

20 Claims, 14 Drawing Sheets

(51) Int. Cl.
    *F16B 21/02*     (2006.01)
    *A46B 13/00*     (2006.01)

(56) References Cited

U.S. PATENT DOCUMENTS

| | | | |
|---|---|---|---|
| 11,458,062 B2 * | 10/2022 | Pang | G06K 7/10366 |
| 2016/0126665 A1 | 5/2016 | Yang | |
| 2017/0348127 A1 | 12/2017 | Pathak et al. | |
| 2018/0344497 A1 | 12/2018 | Pathak et al. | |
| 2019/0000224 A1 | 1/2019 | Pellereau | |
| 2022/0378172 A1 * | 12/2022 | Lee | A45D 34/042 |

FOREIGN PATENT DOCUMENTS

| | | |
|---|---|---|
| JP | 2980981 | 11/1999 |
| JP | 2004154557 A1 | 6/2004 |
| JP | 2019005585 A1 | 1/2019 |
| WO | WO 92/08387 A1 | 5/1992 |
| WO | WO 2020/087087 A1 | 4/2020 |

OTHER PUBLICATIONS

Written Opinion of the International Searching Authority issued Nov. 26, 2020 in FR2012204, 6 pages.
International Search Report and Written Opinion of the International Searching Authority issued Jan. 18, 2022 in PCT/US2021/051994, 18 pages.
JP Notice of Reasons for Rejection dated Sep. 3, 2024 for JP Pat. App. 2023-518804. 5 pages.
KR Notice of Grounds of Rejection for KR Pat. App. 10-2023-7009409 dated Jun. 18, 2024. 6 pages.

* cited by examiner

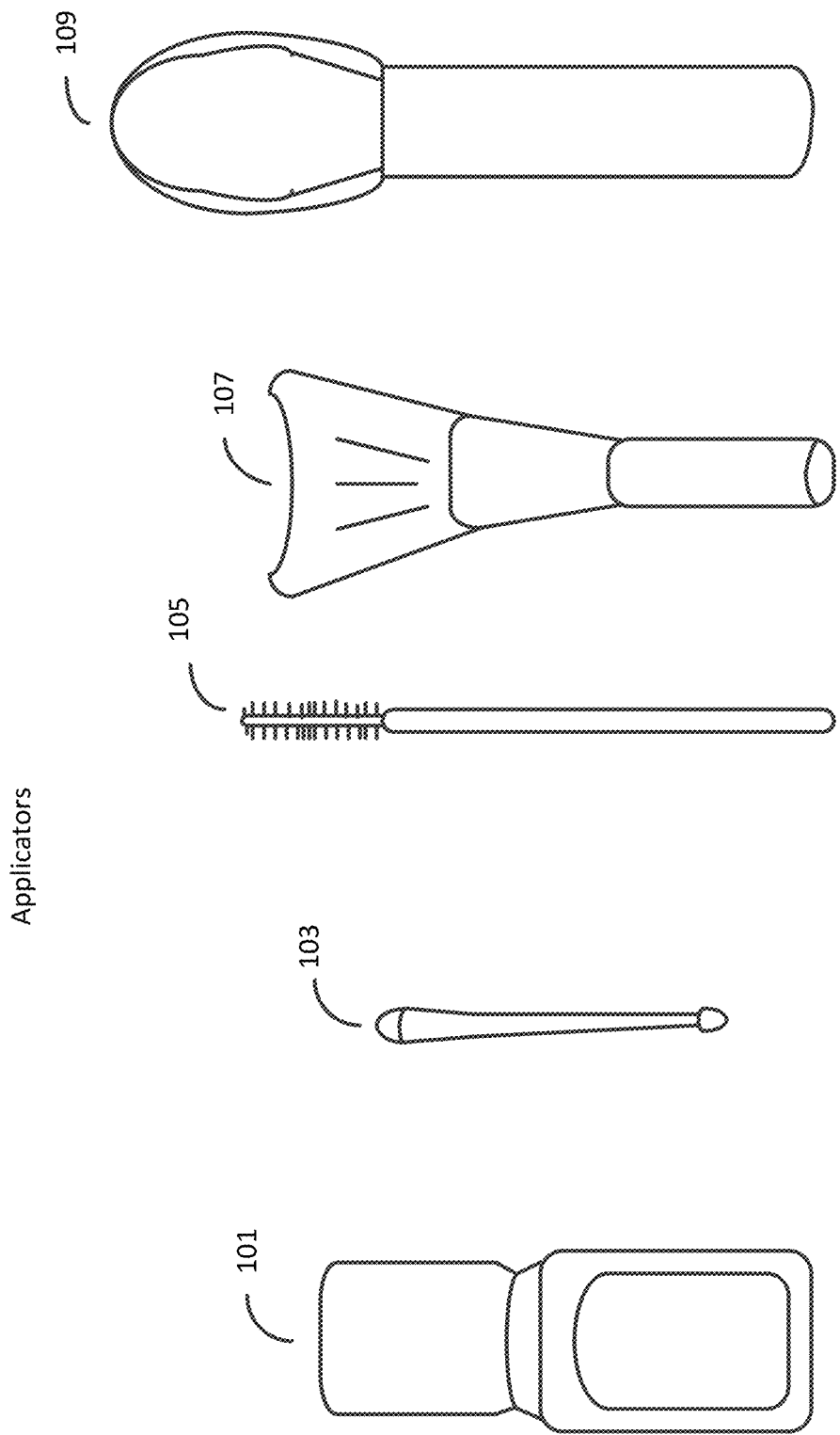

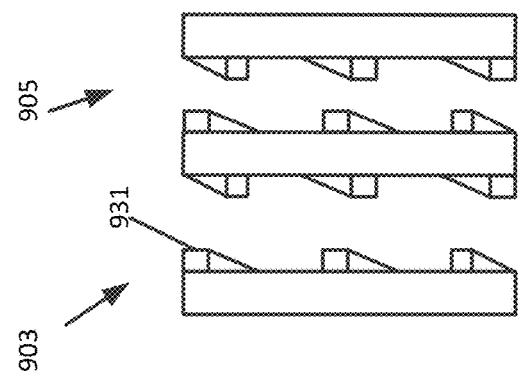
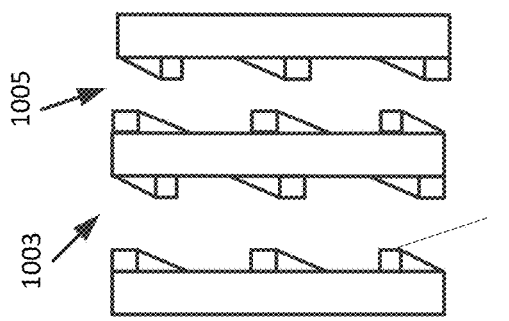
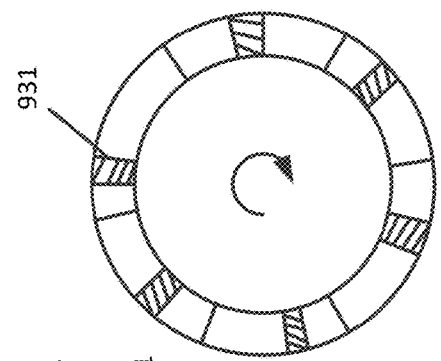
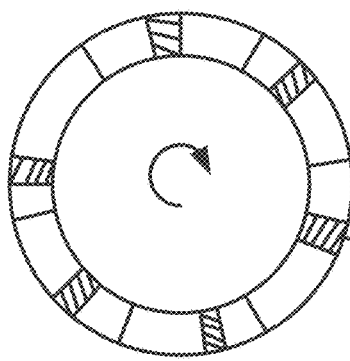
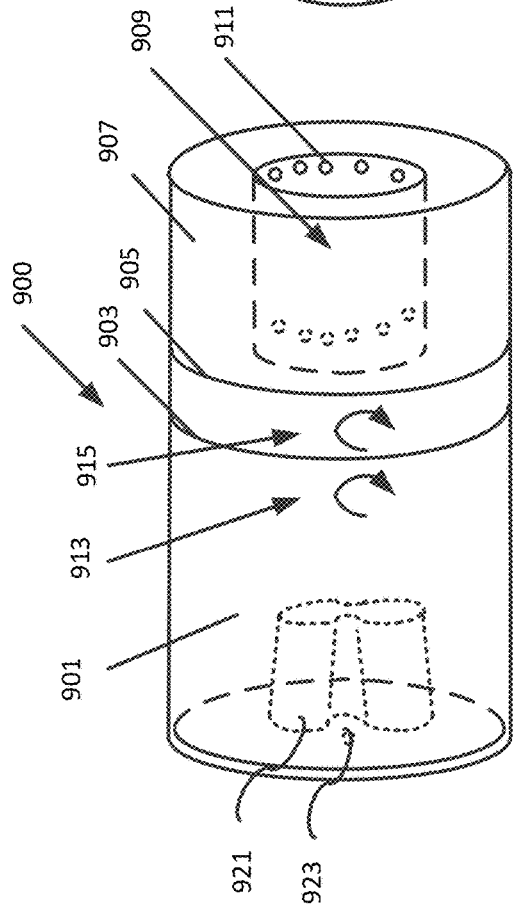
FIG. 9
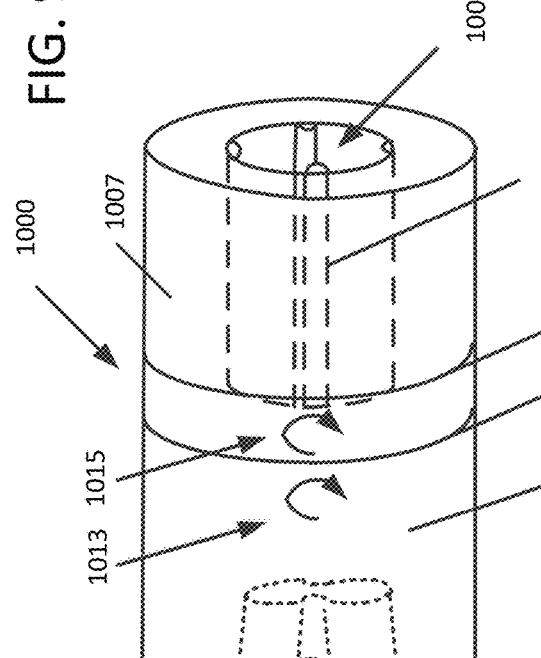
FIG. 10

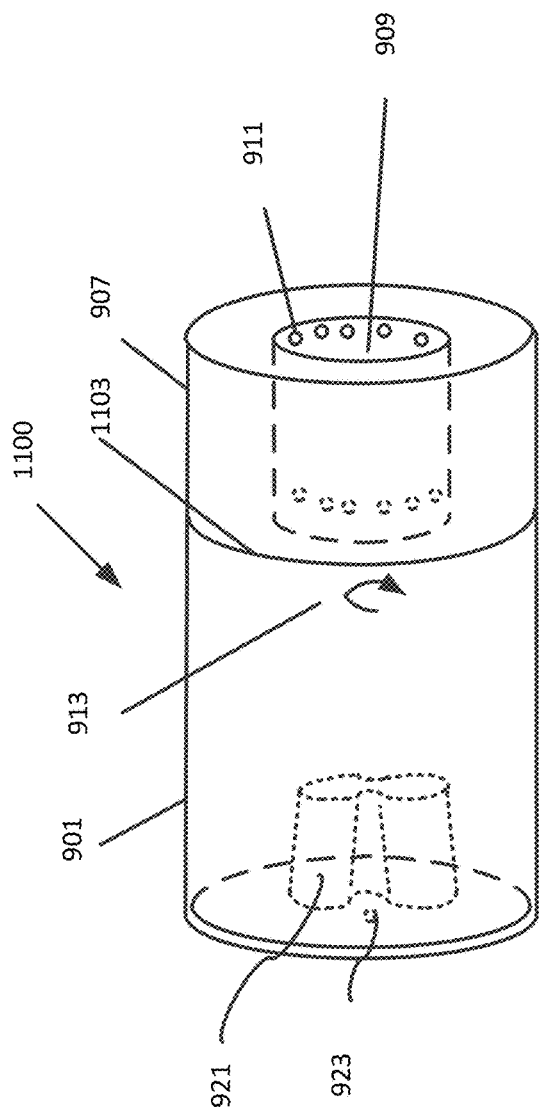
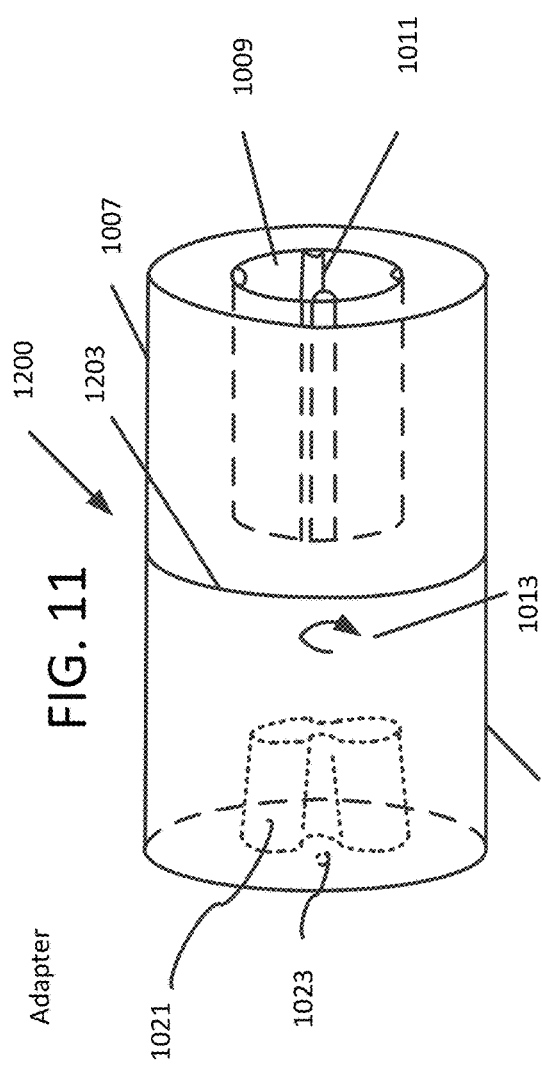
FIG. 11
FIG. 12

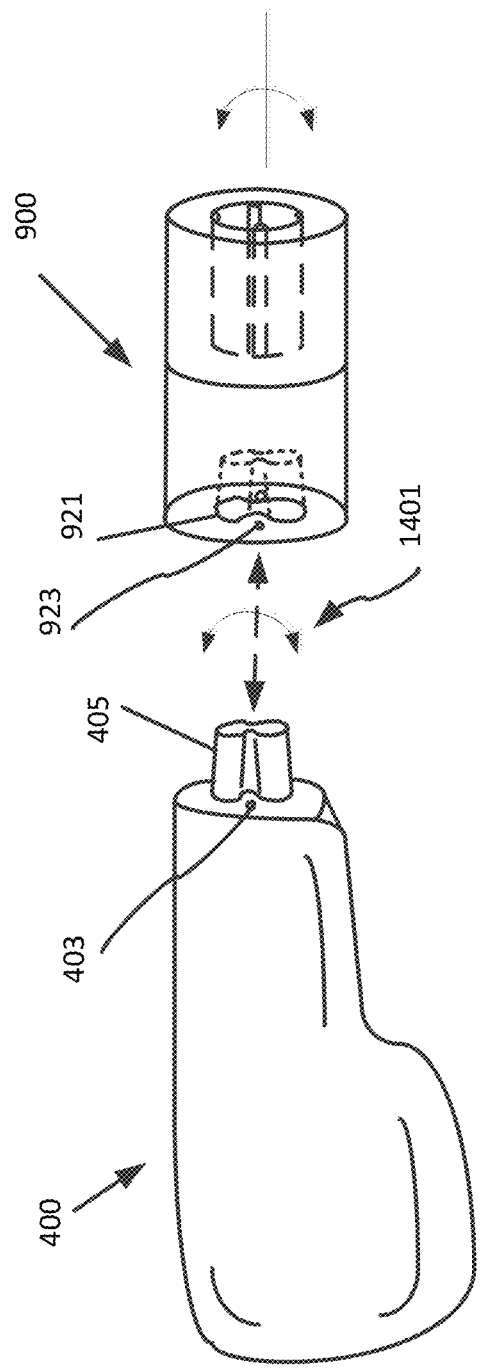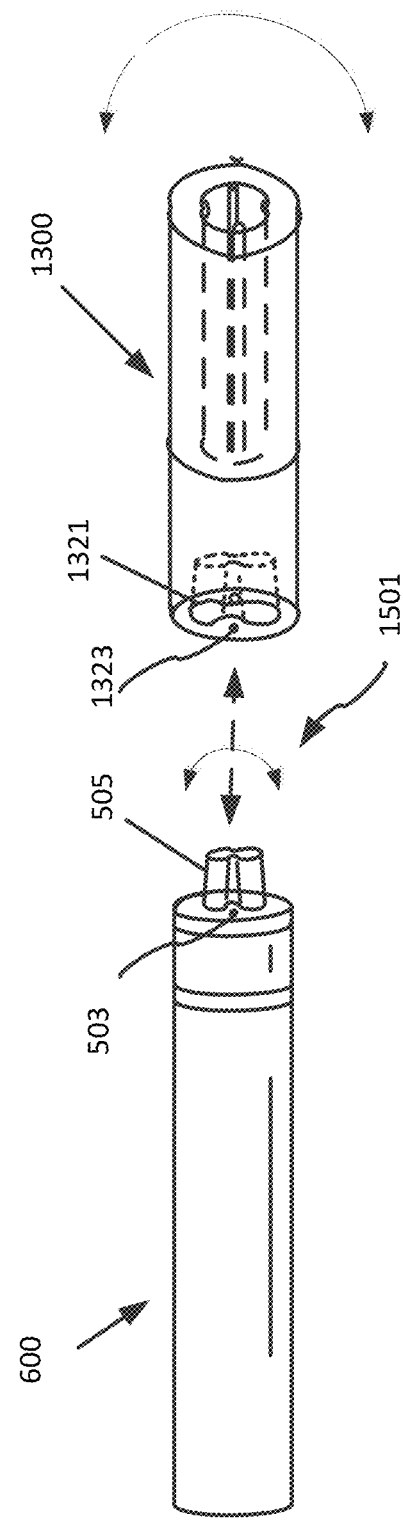
FIG. 14
FIG. 15

ADAPTER WITH INTERCHANGEABLE ELEMENT FOR CONNECTING MAKEUP APPLICATOR TO AN EXTERNAL DEVICE

BACKGROUND

Technical Field

The present disclosure is directed to a interchangeable element for an adapter that connects a makeup applicator to an external device, and in particular a motion controlling device.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

There are many types of makeup applicators, including mascara applicators, lip gloss applicators, eye shadow applicators. Applicators come in wide variety of sizes, shapes and textures.

Conventional mascara applicators include a wand with bristles. The wand includes a stem, with one end of the stem defining an applicator head having the bristles. The applicator head may be a flat comb, a tapered comb, or a curved comb. An applicator head can be thin for shorter lashes, or thick for thicker lashes. Further, applicator heads may have a brush design to promote separation of eyelashes, or another design to promote volume or coverage of eyelashes. The applicator head loaded with mascara is applied to the eyelashes. Mascara application with conventional applicators requires several brush passes.

An end of the stem of the wand may be attached to a handle. The handle is typically a cone shape or cylinder shape, or in some cases a flat rectangular shape. Rotational stem brushes have been proposed that may reduce the need for a user to roll the handle during application of mascara. Rotating mascara brushes may be implemented by supporting a stem of the brush for rotational movement with respect to the handle.

U.S. Pat. No. 8,028,707 to Wyatt et al. describes a cosmetic applicator that includes a handle and a stem, with an applicator head coupled to the stem. An actuator is coupled to the applicator head for moving the applicator head in a vibrational motion.

Despite all of the types of applicator heads, as well as handles that can rotate or vibrate the applicator head, a user with a hand tremor or limited hand and arm mobility may encounter a difficult time using the applicator to apply makeup, particularly makeup that requires fine control such as lip gloss and mascara. A hand tremor may be cased by Parkonson's disease and essential tremor. Person's with a hand tremor will have difficulty holding a makeup applicator steady. Limited hand and arm mobility may be caused by cerebral palsy, spiral cord injury, Huntington's disease, and post stroke defects. Person's with limited hand and arm tremor will have difficulty holding a makeup applicator in a desired position at a certain angle. In addition, the various forms of applicators require different motions of the hand and arm.

It is one object of the present disclosure to describe a combination of a motion stabilizing device or a leveling device and a makeup applicator to assist persons with hand tremors or limited hand and arm mobility. An aspect is an adapter to connect the motion stabilizing device or leveling device to any of several types of makeup applicators of varying sizes and shapes. An aspect is an adapter with one or more rotating elements to allow for ease of adjusting the angle of the makeup applicator.

SUMMARY

An aspect is an adapter that connects any one of a variety of makeup applicators for applying makeup to a motion controlling device that directs movement of the makeup applicator, including a base component having a base connection for connecting the adapter to the motion controlling device in a certain orientation; and an end component having an end connection for connecting the adapter to a makeup applicator. The end component has a center axis through its center and is rotatably attached about the center axis to the base component with a structure for locking the end component in a certain rotated angle about the center axis.

An aspect is a makeup applicator system, including an applicator stabilizer unit configured to stabilize an applicator in response to unintentional muscle motion caused by a user; and an applicator coupling element configured to removably-attach a makeup applicator to the applicator stabilizer unit.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIGS. 1A, 1B, 1C, 1D, 1E are schematics illustrating some different types of makeup applicators over a range of shapes and sizes;

FIG. 9 is a perspective view of an applicator coupling element with multiple detents for rotation of the element in accordance with an exemplary aspect of the disclosure;

FIG. 10 is a perspective view of an alternative applicator coupling element with multiple detents for rotation of the element in accordance with an exemplary aspect of the disclosure;

FIG. 11 is a perspective view of an applicator coupling element with a single detent for rotation in accordance with an exemplary aspect of the disclosure;

FIG. 12 is a perspective view of an alternative applicator coupling element with a single detent for rotation in accordance with an exemplary aspect of the disclosure;

FIG. 14 is a schematic diagram showing a connection relationship for a motion stabilizing device and an applicator coupling element in accordance with an exemplary aspect of the disclosure;

FIG. 15 is a schematic diagram showing a connection relationship for a leveling device or an applicator stabilizer unit and an applicator coupling element in accordance with an exemplary aspect of the disclosure;

DETAILED DESCRIPTION

Figures 2A, 2B, 2C, 2D:
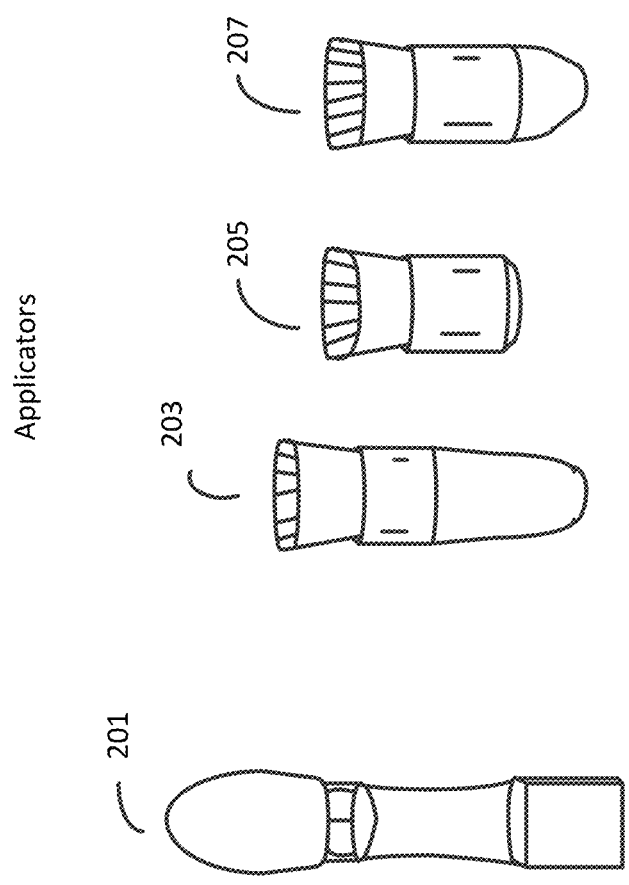
FIGS. 2A, 2B, 2C, 2D are schematics illustrating some different types of makeup applicators over a range of shapes and sizes.

In the drawings, like reference numerals designate identical or corresponding parts throughout the several views. Further, as used herein, the words "a," "an" and the like generally carry a meaning of "one or more," unless stated otherwise. The drawings are generally drawn to scale unless specified otherwise or illustrating schematic structures or flowcharts.

Furthermore, the terms "approximately," "approximate," "about," and similar terms generally refer to ranges that include the identified value within a margin of 20%, 10%, or preferably 5%, and any values therebetween.

Aspects of this disclosure are directed to an applicator coupling element, also referred to as an adapter, that connects any of a variety of types of makeup applicators to a motion stabilizer device, a leveling device, or an applicator stabilizer unit.

In order to provide universal connection of various shapes and sizes of makeup applicators, the applicator coupling element (or adapter), is configured to removably-attach the makeup applicator to the applicator stabilizer unit via a bayonet coupling, a friction fit coupling, a magnetic coupling, a snap fit coupling, or a threaded coupling.

FIGS. 1A, 1B, 1C, 1D, 1E are schematics illustrating some different types of makeup applicators over a range of shapes and sizes. FIG. 1A is a wide-form applicator that may be used for application of creamy foundations, masks, bases or foundations. FIG. 1B is a fine tip swab applicator that may be used for glosses or eyeliners. FIG. 1C is an applicator having a brush at its tip for application of eye mascara. FIG. 1D is brush applicator for application of face makeup or eye makeup. A brush may be small, medium or large and are round, square or tapered. FIG. 1E is a flat puff applicator for application of powder, body shimmer or talcum powder.

FIGS. 2A, 2B, 2C, 2D are schematics illustrating some different types of makeup applicators over a range of shapes and sizes. Some makeup applicators, especially those with brushes and puffs may have large diameter handles. The handles may be shaped, as in FIG. 2A for easy handling, or may be cylindrical with long cone-shaped ends, as in FIG. 2B, capped ends, as in FIG. 2C, or short cone-shaped ends, as in FIG. 2D.

Figure 3A:
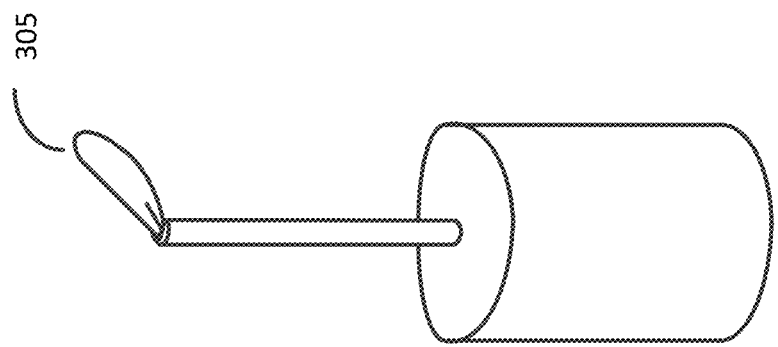
FIGS. 3A, 3B, 3C are schematics illustrating makeup applicators that are inserted in handles.
Figure 3B:
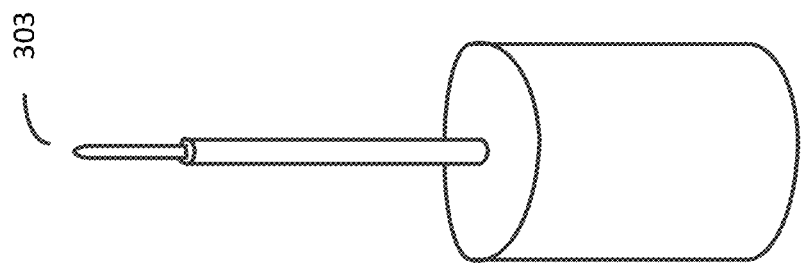
Figure 3C:
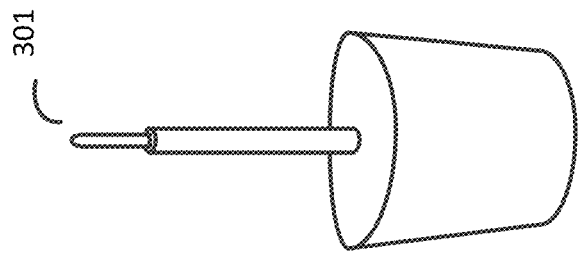

FIGS. 3A, 3B, 3C are schematics illustrating makeup applicators that are inserted in handles. The applicators may be lip gloss brushes or mascara applicators. The handles may be tapered, as in FIG. 3A, or cylindrical, as in FIGS. 3B and 3C.

Figure 4:
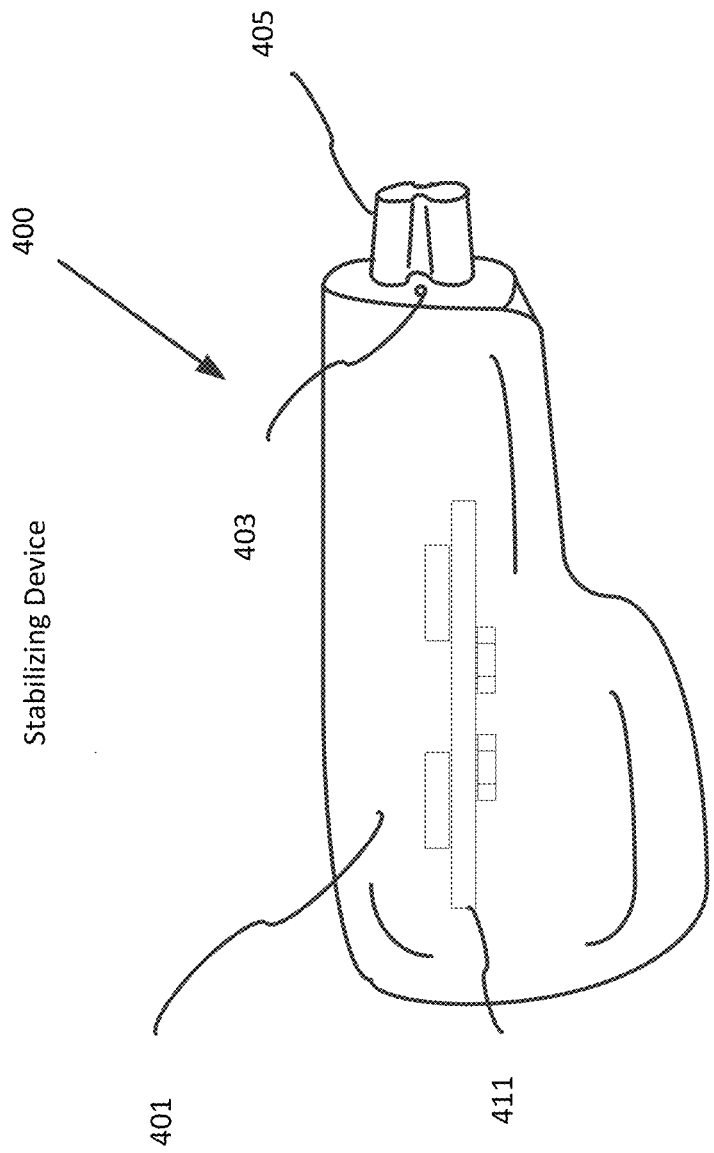
FIG. 4 is a schematic illustrating a motion stabilizing device.

FIG. 4 is a schematic illustrating a motion stabilizing device. The motion stabilizing device 400 may include a handle 401 for easily holding the device, as well as a pair of magnets 403 on either side of a connection component 405. The shape of the connection component 405 and the orientation of the two magnets 403 ensures a one-way connection orientation with an external device. The motion stabilizing device may include a circuit board 411 containing sensors, a controller and motors that control movement of the connection component 405 relative to the movement of a detected tremor. The sensors detect hand motion and the controller distinguishes unwanted tremor from the intended movement of the hand. To stabilize the makeup applicator, the controller directs the motors to move the makeup applicator in the opposite direction of any detected tremor.

Figure 5:
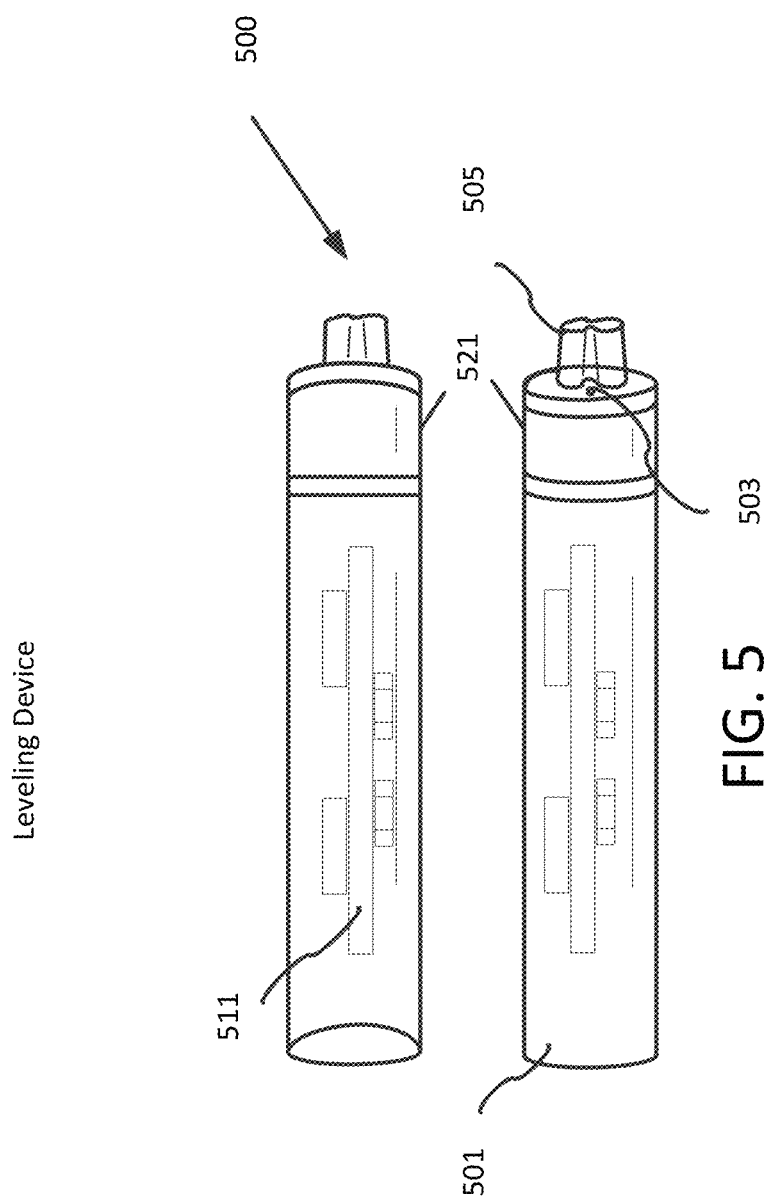
FIG. 5 is a schematic illustrating a leveling device.

FIG. 5 is a schematic illustrating a leveling device. The leveling device 500 includes a cylindrical portion 501, a pair of magnets 503 on either side of a connector 505. The shape of the connector 505 and the orientation of the two magnets 503 ensures a one-way connection orientation with an external device. The leveling device may include a circuit board 511 containing sensors, a controller and motors that control movement of a connection component 521 to keep it level over a range of motion of the leveling device. The sensors detect changes from the intended movement of the hand in 3 dimensions. To level the makeup applicator, the controller directs the motors to bend a flexible joint, keeping the attached makeup applicator at the right angle.

Figure 6:
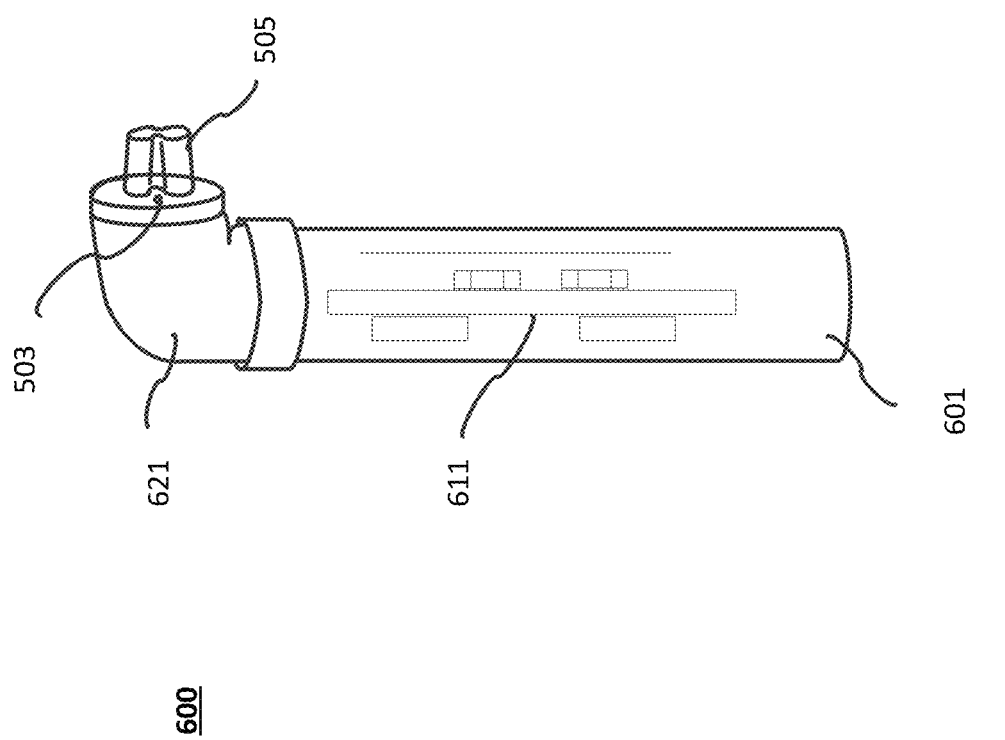
FIG. 6 is a schematic illustrating the applicator stabilizer unit in an angled posture.
Figure 7:
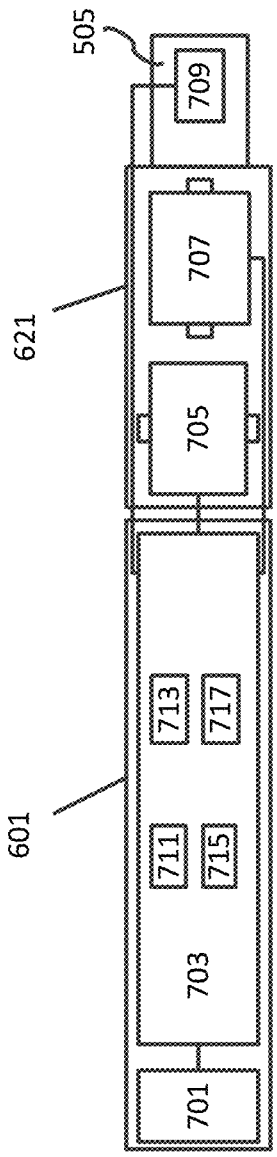
FIG. 7 is a diagram of internal components of the applicator stabilizer unit of FIG. 6.

FIG. 6 is a schematic illustrating the applicator stabilizer unit in an angled posture. U.S. PG Publication 2020/0085168A1, incorporated herein by reference, describes the applicator stabilizer unit in more detail. As shown in FIG. 6, the connection component 621 of the applicator stabilizer unit 600 is configured to contort between an upright posture and an angled posture (as shown in FIG. 6). This is accomplished with a hinge mechanism contained inside the connection component 621. FIG. 6 shows that the hinge mechanism is a self-leveling/motion stabilizing hinge. FIG. 7 is a diagram of internal components of the applicator stabilizing unit of FIG. 6. FIG. 7 shows a diagram of the internal components of applicator stabilizer unit 600 according to one embodiment. In the handle portion 601, the unit includes a power source 701, which may be a battery or the like. The applicator stabilizer unit 600 includes a printed circuit board assembly (PCBA) 703, which may include positional sensor circuitry 711, reader circuitry 713, control circuitry 715, and communication interface 717, as understood in the art.

For instance, as the sensor circuitry 711, the PCBA may include at least one inertial sensor and at least one distributed motion sensor to detect unintentional muscle movements and measure signals related to these unintentional muscle movements that are created when a user adversely affects motion of the makeup applicator. These sensors also detect the motion of the stabilized output relative to the unit. The control circuitry sends voltage commands in response to the signals to the motion generating elements to cancel the user's tremors or unintentional muscle movements. This cancellation maintains and stabilizes a position of the applicator, keeping it stable.

One of ordinary skill in the art readily recognizes that a system and method in accordance with the present invention may utilize various implementations of the control circuitry and the sensor circuitry and that would be within the spirit and scope of the present invention. In one embodiment, the control circuitry 715 comprises an electrical system capable of producing an electrical response from sensor inputs such as a programmable microcontroller or a field-programmable gate array (FPGA). In one embodiment, the control circuitry comprises an 8-bit ATMEGA8A programmable microcontroller manufactured by Atmel due to its overall low-cost, low-power consumption and ability to be utilized in high-volume applications.

In one embodiment, the at least one inertial sensor in the sensor circuitry is a sensor including but not limited to an accelerometer, gyroscope, or combination of the two. In one embodiment, the at least one distributed motion sensor in the sensor circuitry is a contactless position sensor including but not limited to a hall-effect magnetic sensor.

The system created by the combination of the sensor circuitry, the control circuitry, and the motion generating elements may be a closed-loop control system that senses motion and acceleration at various points in the system and feeds detailed information into a control algorithm that moves the motion-generating elements appropriately to cancel the net effect of a user's unintentional muscle movements and thus stabilize the position of the makeup applicator. The operation and details of the elements of the control system and control algorithm are understood in the art, as described in U.S. PG Publication 2014/0052275A1, incorporated herein by reference.

The communication interface 717 may include a network controller such as BCM43342 Wi-Fi, Frequency Modulation, and Bluetooth combo chip from Broadcom, for interfacing with a network.

In the connection component 621 of the applicator stabilizer unit 600, there may be two motive elements to allow 3-dimensional movement of the receiver as anti-shaking movement. The two motive elements include a y-axis motive element 705 and an x-axis motive element 707, each being connected to and controlled by the PCBA 703. Each of the motive elements may be servo motors as understood in the art. The applicator stabilizer unit 600 further includes connector 505, which is configured to couple with an adaptor. The connector 505 may include a radiofrequency identification (RFID) reader 709, configured to read an RFID tag, which may be included with the makeup applicator.

Figure 8:
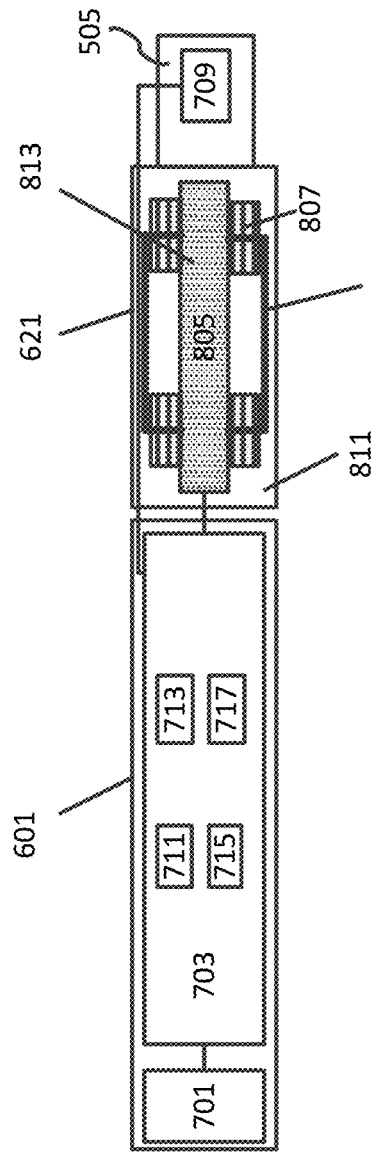
FIG. 8 is a diagram of an alternative configuration of internal components of the applicator stabilizer unit of FIG. 6.

FIG. 8 is a diagram of an alternative configuration of internal components of the applicator stabilizer unit of FIG. 6. FIG. 8 shows a diagram of an alternative embodiment of the applicator stabilizer unit 600 in which the connection component 621 includes an electromagnetic positioner 811 instead of the motive elements shown in FIG. 7. The electromagnetic positioner 811 may include U-shaped magnetic cores 809 arrayed around a non-magnetic tube 805, which is filled with a magnetic fluid 813. Each of the magnetic cores has arm portions that are surrounded by windings 807. The magnetic cores may be controlled by the control circuitry in the PCBA 703 to act as a controllable active magnetic field-generating structure which is used to generate a variable magnetic field that acts upon the magnetic fluid, causing it to be displaced, thereby enabling the armature to be moved to a desired coordinate position and/or orientation. The details of implementing the electromagnetic positioner 811 may be found in U.S. Pat. No. 6,553,161, which is incorporated herein by reference. An applicator coupling element may be configured to removably-attach a makeup applicator to the applicator stabilizer unit. The applicator coupling element may be configured to removably-attach the makeup applicator to the applicator stabilizer unit by any of several types of connections including but not limited to a bayonet coupling, a friction fit coupling, a magnetic coupling, a snap fit coupling, or a threaded coupling.

The applicator coupling element may include at least of first attachment portion configured to removably-attach a makeup applicator to the applicator coupling element, and a second attachment portion configured to removably-attach the applicator coupling element to the applicator stabilizer unit. The first attachment portion removably-attaches to the applicator via one of a bayonet coupling, a friction fit coupling, a magnetic coupling, a snap fit coupling, or a threaded coupling; and the second attachment portion removably-attaches to the applicator stabilizer unit via a different one of a bayonet coupling, a friction fit coupling, a magnetic coupling, a snap fit coupling, or a threaded coupling.

The applicator coupling element may include at least of first attachment portion configured to removably-attach a makeup applicator to the applicator coupling element, and a second attachment portion configured to removably-attach the applicator coupling element to the applicator stabilizer unit. The first attachment portion and the second attachment portion include a bayonet coupling component, a friction fit coupling component, a magnetic coupling component, a snap fit coupling component, or a threaded coupling component.

FIG. 9 is a perspective view of an applicator coupling element (adapter) with multiple detents for rotation of the element in accordance with an exemplary aspect of the disclosure. The applicator coupling element 900 may have a diameter that is sufficient for mounting makeup applicators that are inserted into handles. A base portion 901 may include an opening 921 of a shape to receive the connection component 405 of the motion stabilizing device 400. Although the drawing in FIG. 9 shows the opening as having an hour glass cross section, the opening may be of other shapes, including but not limited to, elliptical.

The base portion 901 may include a pair of magnets 923 to ensure correct orientation of the applicator coupling element 900 with the motion stabilizing device 400. In particular, the polarization of the magnets 923 may be such that in the proper orientation, the magnets 403 will be attracted to the corresponding magnets 923. In an improper orientation, the magnets 403 will be repelled by the magnets 923. The magnetic force between the magnets 923 and 403 is used to hold the applicator coupling element 900 to the motion stabilizing device 400. The base portion 901 has a cylindrical exterior shape for ease combining with the end portion 907. The base portion 901 may take alternative shapes including an hour glass shape or tapered shape to accommodate an end portion 907 of a reduced or enlarged diameter.

The applicator coupling element 900 includes multiple detents to allow for fine adjustment of the angle at which the applicator is positioned relative to the motion stabilization device 400. Regarding FIG. 9, a first detent 903 allows rotation 913 relative to the base portion 901. A second detent 905 allows rotation 915 relative to the first detent 903. The detents may include one or more springs to apply force on the detents. The first and second detents 903, 905 may be configured as a locking detent having an arrangement of evenly spaced catches 931 around the circumference of a ring. The catches 931 allow a one-way rotation direction 913. The amount of angle rotation between lock positions depends on the number of catches 931. Having two detents 903, 905 may allow an angle of rotation between lock positions to be cut in half, enabling a finer degree of control. In one embodiment the catches 931 are wedge shaped to allow for ease of rotation between lock positions. In an alternative embodiment, the catches are rectangular tooth-shaped that insert into slots of an end tooth arrangement of a corresponding component. The detents 903, 905 and base 901 may be made of plastic or a metal alloy such as stainless steel or aluminum.

An opening 909 in an end portion 907 is shaped and sized to accept a makeup applicator having a handle. The opening 909 may have a circular cross section such that the opening 909 is cylindrical. In some embodiments, the opening 909 may have a rectangular cross section. To hold a makeup applicator in place, bumps 911 may be arranged inside the opening 909. The bumps 911 may be evenly spaced in a linear arrangement around the inner circumference of the opening. More than one linear arrangement may be provided along the depth of the opening. The bumps 911 may be randomly arranged in the inner surface of the opening. The end portion 907 may be made of a soft compressible material such as rubber. In some embodiments, the bumps 911 may be rubber. In some embodiments, the bumps 911 may be positioned to accommodate makeup applicators of different shapes and sizes. In some embodiments, the opening 909 may be tapered to a smaller cross section relative to an entrance to the opening 909.

FIG. 10 is a perspective view of an alternative applicator coupling unit (adapter) with multiple detents for rotation of the applicator coupling element in accordance with an exemplary aspect of the disclosure. Similar to the applicator coupling element 900, the applicator coupling element 1000 includes a base portion 1001 may include an opening 1021 of a shape to receive the connection component 405 of the motion stabilizing device 400. The base portion 1001 may include a pair of magnets 1023 to ensure correct orientation of the adapter 1000 with the motion stabilizing device 400. In particular, the polarization of the magnets 1023 may be such that in the proper orientation, the magnets 403 will be attracted to the corresponding magnets 1023. In an improper orientation, the magnets 403 will be repelled by the magnets 1023. The magnetic force between the magnets 1023 and 403 is used to hold the adapter 1000 to the motion stabilizing device 400.

The applicator coupling unit 1000 includes multiple detents to allow for fine adjustment of the angle at which the makeup applicator is rotated relative to a central axis of the motion stabilization device 400. Regarding FIG. 10, a first detent 1003 allows rotation 1013 relative to the base portion 1001. A second detent 1005 allows rotation 1015 relative to the first detent 1003. The first and second detents 1003, 1005 may be configured as a locking detent having an arrangement of evenly spaced catches 1031 around the circumference of a ring. The catches 1031 allow a one-way rotation. In one embodiment the catches 1031 are wedge shaped. In an alternative embodiment, the catches are rectangular tooth-shaped that insert into slots of an end tooth arrangement of a corresponding component. The detents 1003, 1005 and base 1001 may be made of plastic.

An opening 1009 in an end portion 1007 is sized to accept a makeup applicator having a handle. To hold a makeup applicator in place, ribs 1011 may be arranged inside the opening 1009. The ribs 1011 may be evenly spaced in a circular arrangement around the inner circumference of the opening. The ribs 1011 may extend the entire depth of the opening. The end portion 1007 may be made of a soft compressible material such as rubber.

FIG. 11 is a perspective view of an applicator coupling unit (adapter) with a single detent for rotation in accordance with an exemplary aspect of the disclosure. The applicator coupling element 1100 is similar in structure to the applicator coupling element 900, but includes only a single detent 1103.

FIG. 12 is a perspective view of an alternative applicator coupling element (adapter) with a single detent for rotation in accordance with an exemplary aspect of the disclosure. The applicator coupling element 1200 is similar in structure to the applicator coupling element 1000, but includes only a single detent 1203.

Figure 13:
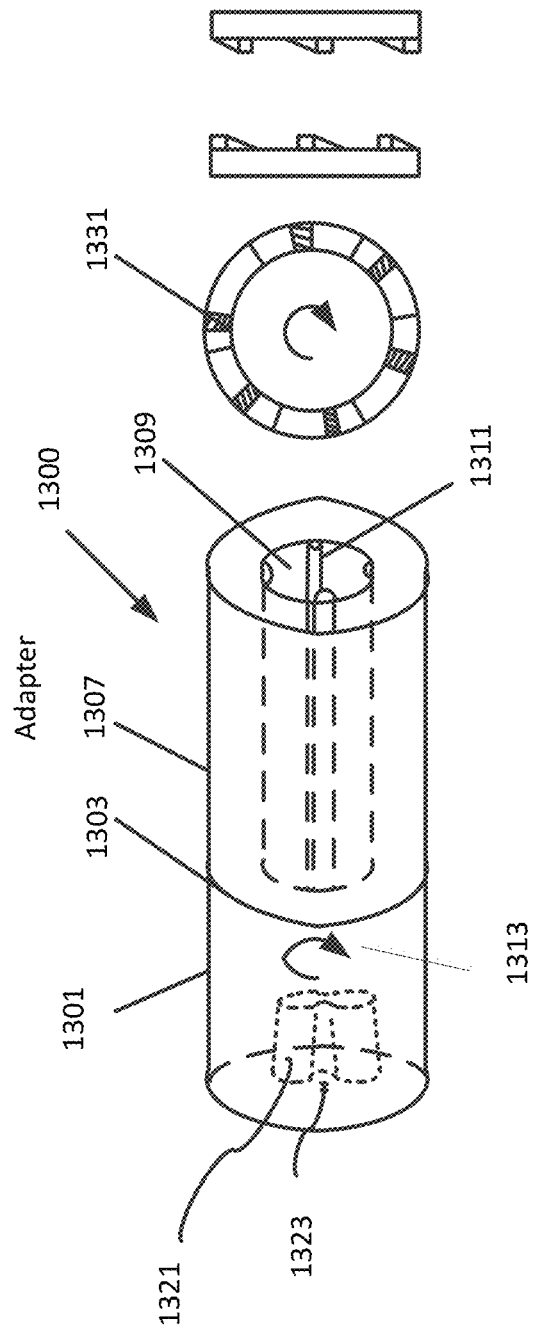
FIG. 13 is a perspective view of an alternative applicator coupling element having a smaller diameter than the adapters of FIGS. 9-12.

FIG. 13 is a perspective view of an alternative applicator coupling element (adapter) having a smaller diameter than the elements of FIGS. 9-12. The applicator coupling element 1300 may be of a smaller diameter to accommodate a leveler or stabilizing device that has a smaller connection interface. Similar to the elements 900, 1000, 1100, 1200, the applicator coupling element 1300 includes a base portion 1301 may include an opening 1321 of a shape to receive the connection component 505 of the applicator stabilizer unit 500. The base portion 1301 may include a pair of magnets 1323 to ensure correct orientation of the applicator coupling element 1300 with the applicator stabilizer unit 500. In particular, the polarization of the magnets 1323 may be such that in the proper orientation, the magnets 503 will be attracted to the corresponding magnets 1323. In an improper orientation, the magnets 503 will be repelled by the magnets 1323. The magnetic force between the magnets 1323 and 503 is used to hold the applicator coupling element 1300 to the applicator stabilizer unit 500.

The applicator coupling element 1300 may include a detent to allow for adjustment of the angle at which the makeup applicator is positioned relative to the applicator stabilizer unit 500. In some embodiments, the applicator coupling element 1300 may include multiple detents for fine adjustment of the rotation angle of the makeup applicator. Regarding FIG. 13, a detent 1303 allows rotation 1313 relative to the base portion 1301. The detents 1305 may be configured as a locking detent having an arrangement of evenly spaced catches 1331 around the circumference of a ring. The catches 1331 allow a one-way rotation. In one embodiment the catches 1331 are wedge shaped. In an alternative embodiment, the catches are rectangular tooth-shaped that insert into slots of an end tooth arrangement of a corresponding component. The detent 1303 and base 1301 may be made of plastic.

An opening 1309 in an end portion 1307 is sized to accept a small diameter makeup applicator such as a wand. To hold a makeup applicator in place, ribs 1311 may be arranged inside the opening 1309. The ribs 1311 may be evenly spaced in a circular arrangement around the inner circumference of the opening. The ribs 1311 may extend the entire depth of the opening. The end portion 1307 may be made of a soft compressible material such as rubber.

FIG. 14 is a schematic diagram showing a connection relationship for a motion stabilizing device and an applicator coupling element in accordance with an exemplary aspect of the disclosure. The magnetic force between the magnets 923 and 403 is used to hold the applicator coupling element 900 to the motion stabilizing device 400 when the connector 405 is inserted into the opening 921. The motion stabilizing device 400 is configured to apply a motion to the connector 405 which causes a vertical angular motion 1401 of the applicator coupling element 900.

FIG. 15 is a schematic diagram showing a connection relationship for a leveling device or an applicator stabilizer unit and an applicator coupling element in accordance with an exemplary aspect of the disclosure. The magnetic force between the magnets 1323 and 503 is used to hold the applicator coupling element 1300 to the leveling device 500 or applicator stabilizer unit 600 when the connector 505 is inserted into the opening 1321. The leveling device 500 is configured to apply a motion to the connector 505 which causes a vertical angular motion 1501 of the applicator coupling element 1300. The vertical angular motion 1501 is a wider range of motion than the motion 1401 as the motion allows the applicator coupling element 1300 to remain level over a range of orientations of the leveling device.

Figure 16:
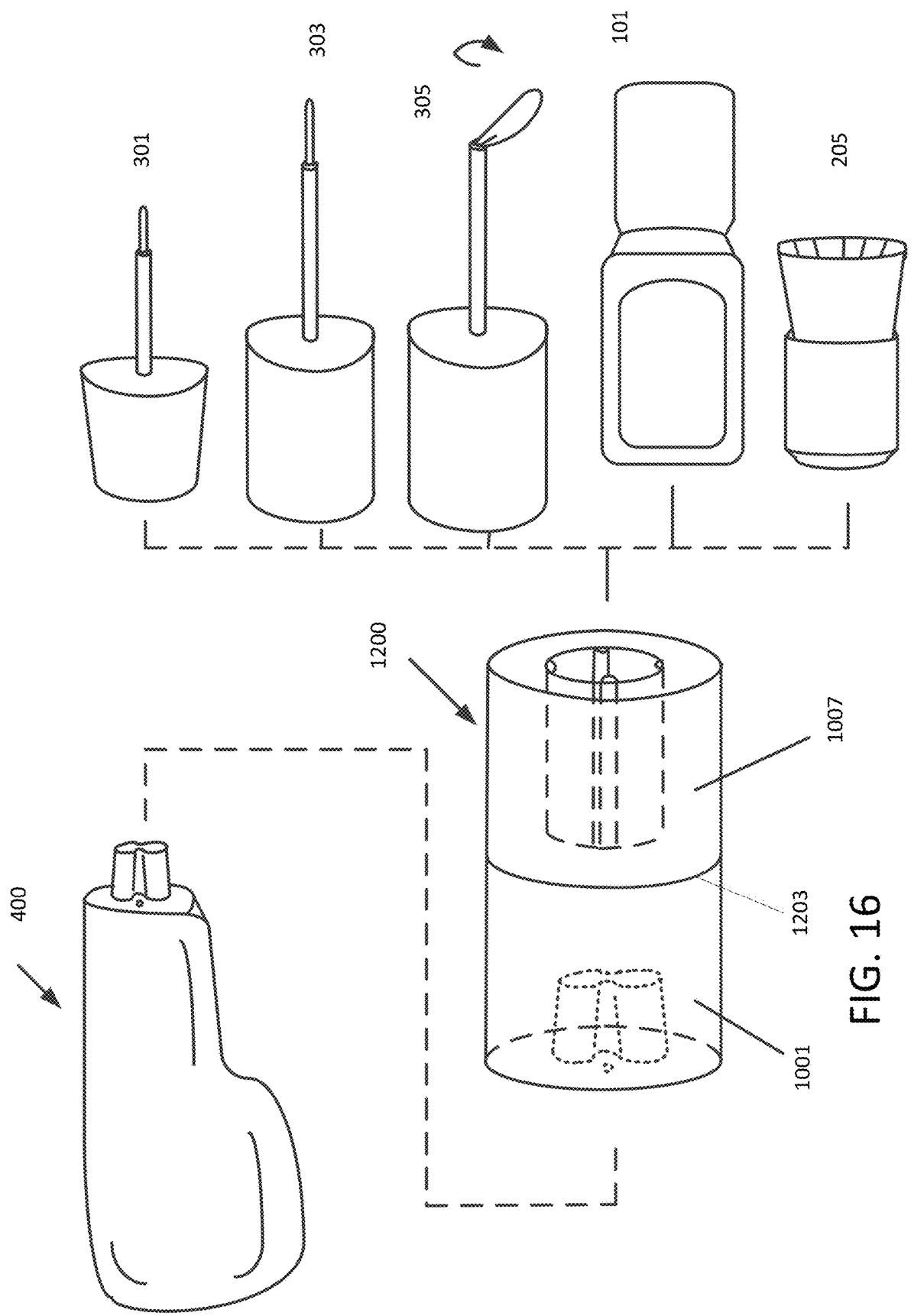
FIG. 16 is a schematic diagram showing a connection relationship for a motion stabilizing device, applicator coupling element and makeup applicators in accordance with an exemplary aspect of the disclosure.

FIG. 16 is a schematic diagram showing a connection relationship for a motion stabilizing device, applicator coupling element (adapter) and makeup applicators in accordance with an exemplary aspect of the disclosure. The applicator coupling element (adapter) 900, 1000, 1100, 1200 may be used to join makeup applicators that have a wide diameter, such as applicators 101, 205, or are mounted to a handle of wide diameter, such as 301, 303, 305, to the motion stabilizing device 400. The detent 903 allows the applicator coupling element 900, 1000, 1100, 1200 to be rotated and locked at a rotate angle 1013. Multiple detents may be used to allow a finder control over the rotation angle 1013.

Figure 17:
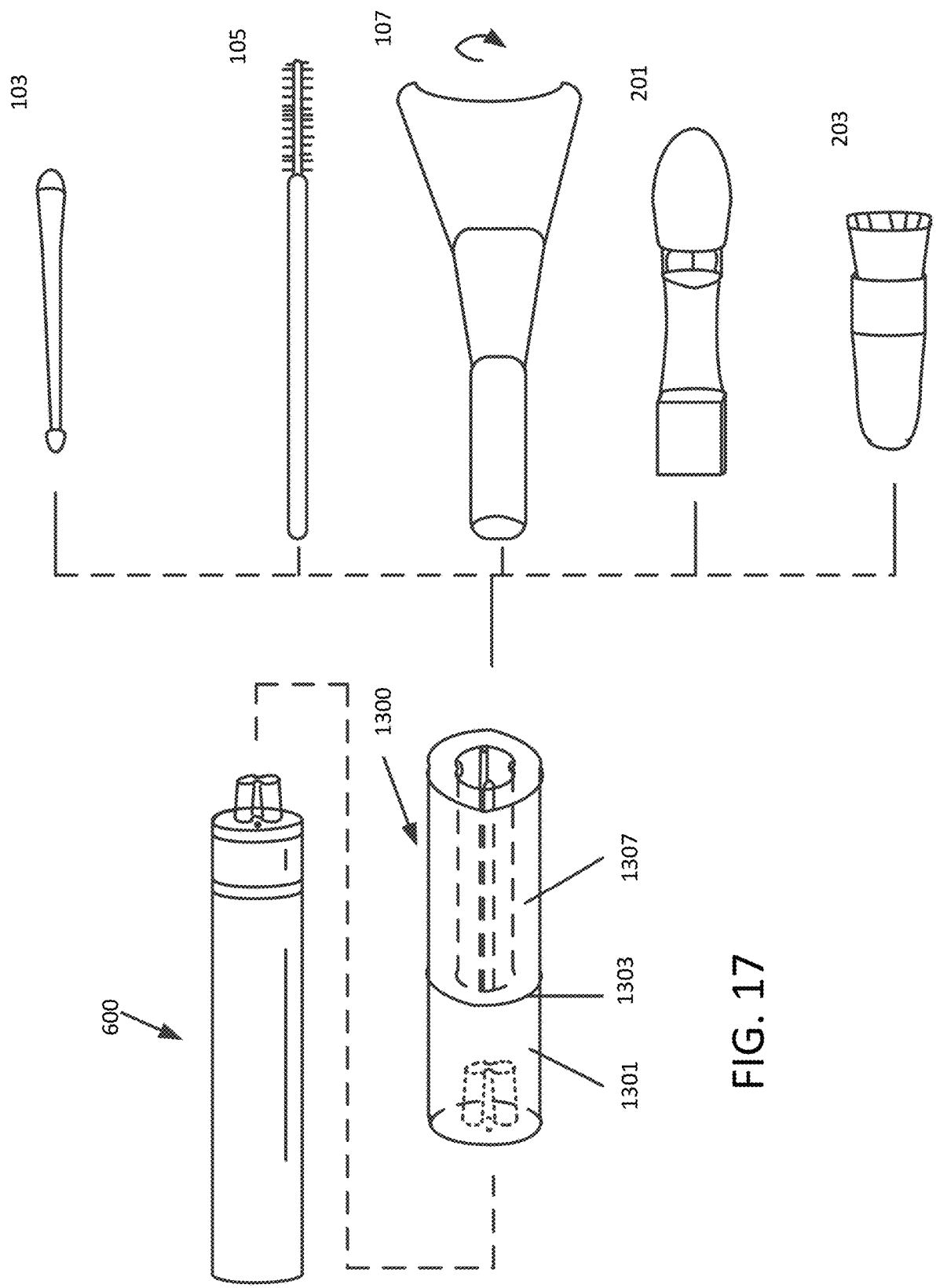
FIG. 17 is a schematic diagram showing a connection relationship for a leveling device or an applicator stabilizer unit, applicator coupling element and makeup applicators in accordance with an exemplary aspect of the disclosure.

FIG. 17 is a schematic diagram showing a connection relationship for a leveling device or an applicator stabilizer unit, applicator coupling element (adapter) and makeup applicators in accordance with an exemplary aspect of the disclosure. The applicator coupling element (adapter) 1300 may be used to join makeup applicators, such as applicators 103, 105, 107, 201, 203, to the leveling device 500 or applicator stabilizer unit 600. The detent 1303 allows the applicator coupling element 1300 to be rotated and locked at a rotation angle 1313.

The applicator coupling elements 900, 1000, 1100, 1200, 1300 may be provided in various sizes so that the motion stabilizing device 400 may be used with makeup applicators of small diameters, or so that the applicator stabilizer unit 1300 may be used with makeup applicators of large diameters or inserted into handles.

Figure 18C:
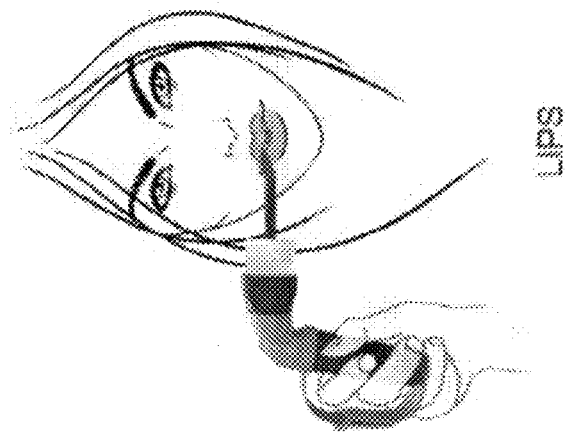
FIGS. 18A, 18B, 18C illustrate different examples of using the applicator stabilizer unit with different applicators.
Figure 18B:
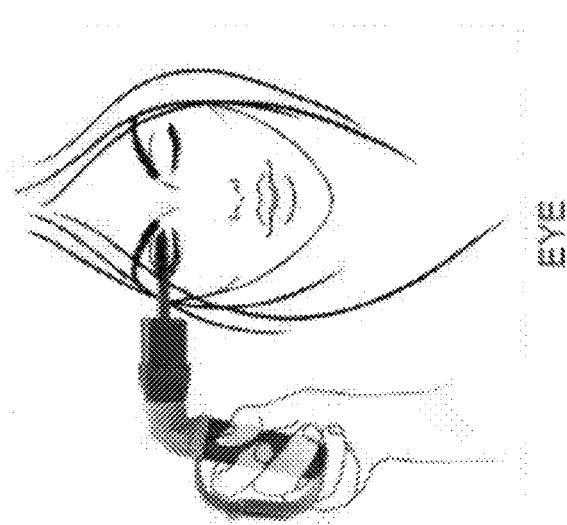
Figure 18A:
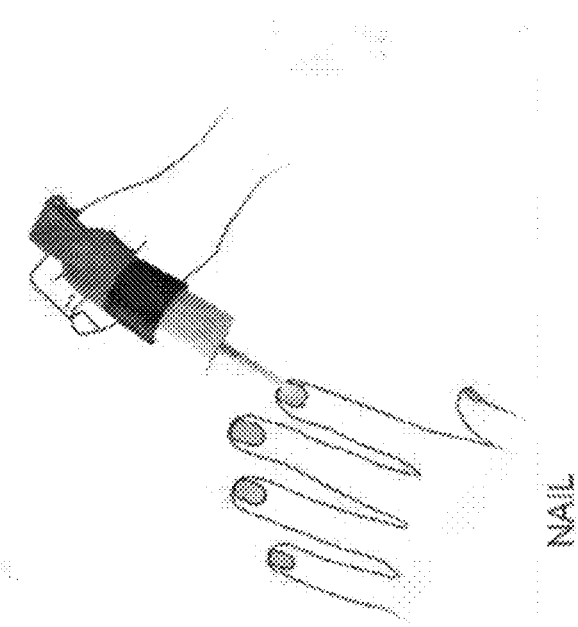

FIGS. 18A-18C show different example of using the applicator stabilizer unit 500 with different applicators, such as a nail polish applicator in 18A, a mascara brush in 18B, and a lipstick applicator in 18C.

Numerous modifications and variations of the present invention are possible in light of the above teachings.

It is therefore to be understood that within the scope of the appended claims, the invention may be practiced otherwise than as specifically described herein.

The invention claimed is:

1. An adapter that connects any one of a variety of makeup applicators for applying makeup to a motion controlling device that directs movement of the makeup applicator, comprising:
   a base component having a base connection for connecting the adapter to the motion controlling device in a certain orientation; and
   an end component having an end connection for connecting the adapter to a makeup applicator;
   wherein the end component has a center axis through its center and is rotatably attached about the center axis to the base component with a structure for locking the end component in a certain rotated angle about the center axis.

2. The apparatus of claim 1, wherein the end component is made of rubber.

3. The apparatus of claim 1, wherein the base connection has a cross section of an elliptical shape.

4. The apparatus of claim 1, wherein the base connection has a cross section of an hourglass shape.

5. The apparatus of claim 1, wherein the base connection includes a pair of magnets positioned at opposite sides of the base connection, and
   wherein the pair of magnets have a first polarization that attracts the motion stabilizing device in one orientation and repels the motion stabilizing device in another orientation.

6. The apparatus of claim 1, wherein the structure for locking the end component in a certain rotated angle about the center axis is a lockable detent that allows incremental rotation in one direction and locks to prevent rotation in a reverse rotation direction.

7. The apparatus of claim 1, wherein the end connection for connecting the adapter to a makeup applicator includes an opening for inserting and holding the makeup applicator within the opening.

8. The apparatus of claim 7, wherein the opening for holding the makeup applicator includes a plurality of rubber bumps protruding inside the opening in order to grasp a makeup applicator.

9. The apparatus of claim 8, wherein the plurality of rubber bumps are arranged in at least two ring patterns.

10. The apparatus of claim 7, wherein the opening for holding the makeup applicator includes a plurality of equally spaced ribs protruding inside the opening extending in a depth direction of the opening in order to grasp the makeup applicator.

11. The apparatus of claim 1, wherein the end component is interchangeable with other end components having openings of different size and shape.

12. The apparatus of claim 1, wherein the motion controlling device directs movement in an opposite direction of any detected hand vibration motion.

13. The apparatus of claim 7, wherein the opening for holding the makeup applicator is cylindrical shape.

14. The apparatus of claim 7, wherein the opening for holding the makeup applicator is tapered to a smaller diameter from an entrance to the opening.

15. The apparatus of claim 7, wherein the opening for holding the makeup applicator is a rectangular cross-section.

16. A makeup applicator system, comprising:
   an applicator stabilizer unit configured to stabilize an applicator in response to unintentional muscle motion caused by a user; and
   an applicator coupling element configured to removably-attach a makeup applicator to the applicator stabilizer unit,
   wherein the applicator coupling element includes a base component having a base connection for connecting the applicator coupling element to the applicator stabilizer unit in a certain orientation,
   wherein the base connection has a cross section of an elliptical shape,
   wherein the applicator coupling element includes an end component for connecting the applicator coupling element to the makeup applicator, and
   wherein the end component is made of rubber.

17. The makeup applicator system of claim 16, wherein the applicator coupling element is configured to removably-attach the makeup applicator to the applicator stabilizer unit via a bayonet coupling, a friction fit coupling, a magnetic coupling, a snap fit coupling, or a threaded coupling.

18. The makeup applicator system of claim 16, wherein the applicator coupling element comprises
- at least of first attachment portion configured to removably-attach a makeup applicator to the applicator coupling element, and
- a second attachment portion configured to removably-attach the applicator coupling element to the applicator stabilizer unit.

19. The makeup applicator system of claim 16, wherein
- the first attachment portion removably-attaches to the applicator via one of a bayonet coupling, a friction fit coupling, a magnetic coupling, a snap fit coupling, or a threaded coupling; and
- the second attachment portion removably-attaches to the applicator stabilizer unit via a different one of a bayonet coupling, a friction fit coupling, a magnetic coupling, a snap fit coupling, or a threaded coupling.

20. The makeup applicator system of claim 16, wherein the applicator coupling element comprises
- at least of first attachment portion configured to removably-attach a makeup applicator to the applicator coupling element, and
- a second attachment portion configured to removably-attach the applicator coupling element to the applicator stabilizer unit; and
- wherein the first attachment portion and the second attachment portion include a bayonet coupling component, a friction fit coupling component, a magnetic coupling component, a snap fit coupling component, or a threaded coupling component.

* * * * *